United States Patent [19]

Wehner et al.

[11] 4,390,538
[45] Jun. 28, 1983

[54] PESTICIDAL TRIORGANO-TIN TRIAZINES

[75] Inventors: Wolfgang Wehner, Zwingenberg, Fed. Rep. of Germany; Saleem Farooq, Ettingen, Switzerland; Hans-Günter Köstler, Heppenheim, Fed. Rep. of Germany

[73] Assignee: Ciba-Geigy Corporation, Ardsley, N.Y.

[21] Appl. No.: 297,884

[22] Filed: Aug. 31, 1981

[30] Foreign Application Priority Data

Sep. 12, 1980 [CH] Switzerland .................... 6882/80

[51] Int. Cl.³ .................. C07D 251/52; C07D 251/34; C07D 251/38; A01N 43/70

[52] U.S. Cl. .................................... 424/249; 544/198; 544/213; 544/204; 544/210; 544/196; 544/218; 544/219; 544/181

[58] Field of Search ............... 544/198, 213, 204, 210, 544/196, 218, 219, 181; 424/249

[56] References Cited

U.S. PATENT DOCUMENTS

| | | | |
|---|---|---|---|
| 3,047,532 | 7/1962 | D'Alelio | 544/219 |
| 3,050,496 | 8/1962 | D'Alelio | 544/219 |
| 3,053,796 | 9/1962 | D'Alelio | 544/219 |
| 3,056,760 | 10/1962 | D'Alelio | 544/219 |
| 4,316,853 | 2/1982 | Gitlitz et al. | 544/181 |

FOREIGN PATENT DOCUMENTS

| | | | |
|---|---|---|---|
| 41-224 | 1/1966 | Japan | 544/181 |
| 42-25905 | 12/1967 | Japan | 544/181 |
| 6907245 | 11/1970 | Netherlands | 544/181 |
| 1122595 | 8/1968 | United Kingdom | 544/181 |

*Primary Examiner*—John M. Ford
*Attorney, Agent, or Firm*—Frederick H. Rabin

[57] ABSTRACT

The invention relates to triorgano-tin triazine compounds of the formula

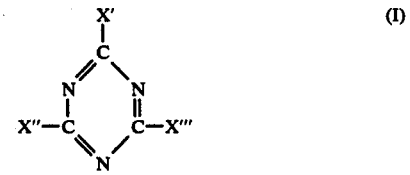

wherein $X'$ is $-S-Y-COOSn(R')_3$, $-O-Y-COOSn(R')_3$ or $-NH-Y-COOSn(R')_3$, each of $X''$ and $X'''$ has the same meaning as $X'$ or is halogen, $(C_1-C_6 \text{ alkyl})_2N-$, $(C_1-C_6 \text{alkyl})-NH-$, $(C_1-C_6 \text{alkyl})-O-$ or $(C_1-C_6 \text{alkyl})-S-$, Y is $C_1-C_6$ alkylene, and the radicals $R'$ can be the same or different and are $C_1-C_6$ alkyl, bennzyl, phenyl or cycohexyl, each of which is unsubstituted or substituted.

A process for the production of thee compounds, starting compounds suitable for this process, and the use of the compounds of formula I in pest control are also described.

12 Claims, No Drawings

PESTICIDAL TRIORGANO-TIN TRIAZINES

The present invention relates to triorgano-tin triazine compounds, to the production thereof and to the use thereof in pest control.

The triorgano-tin triazine compounds have the formula

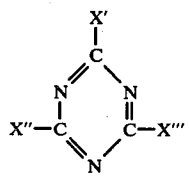

wherein X' is —S—Y—COOSn(R')$_3$, —O—Y—COOSn(R')$_3$ or —NH—Y—COOSn(R')$_3$, each of X" and X'" has the same meaning as X' or is halogen, (C$_1$-C$_6$ alkyl)$_2$N—, (C$_1$-C$_6$alkyl)—NH—, (C$_1$-C$_6$alkyl)—O— or (C$_1$-C$_6$alkyl)—S—, Y is C$_1$-C$_6$alkylene, and the radicals R' can be the same or different and are C$_1$-C$_6$alkyl, benzyl, phenyl or cyclohexyl, each of which is unsubstituted or substituted.

Suitable substituents of benzyl, phenyl or cyclohexyl within the definition of R' are halogen, C$_1$-C$_4$alkyl, C$_1$-C$_4$alkoxy or trifluoromethyl. Halogen denotes fluorine, chlorine, bromine or iodine, with chlorine being preferred. Alkyl groups X", X'" and R' can be straight-chain or branched. Representative examples of such groups are: methyl, ethyl, propyl, isopropyl, n-butyl, isobutyl, sec- or tert-butyl, n-pentyl, n-hexyl, n-decyl or n-dodecyl and the isomers thereof. Methyl, ethyl, isopropyl or propyl are preferred.

Suitable alkylene groups Y can be straight-chain or branched. The preferred identity is methylene.

Preferred compounds of the formula I are those in which X' is —S—Y—COOSn(R')$_3$, each of X" and X'" is (C$_1$-C$_6$alkyl)—NH—, Y is methylene and R' is n-butyl, phenyl or cyclohexyl.

The most preferred compounds of the formula I are those in which X' is —S—Y—COOSn(R')$_3$, each of X" and X'" is (C$_1$-C$_6$alkyl)—NH—, Y is methylene and R' is cyclohexyl.

The compounds of formula I can be obtained by methods which are known per se, e.g. as follows:

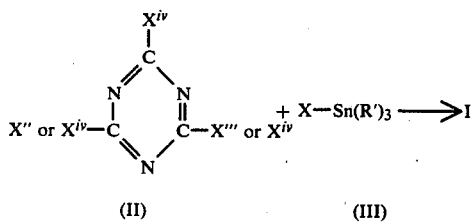

In formulae II and III above, X", X'" and R' are as defined for formula I, X$^{iv}$ is —S—Y—COOH, —O—Y—COOH or —NH—Y—COOH, wherein Y is C$_1$-C$_6$ alkylene and X is a (R')$_3$Sn—O or —OH group or a halogen atom, especially chlorine. Where X is a halogen atom, the reaction must be carried out in the presence of a base as hydrogen halide acceptor. Especially prepared compounds of the formula II are those containing the radicals X", X'" and X$^{iv}$.

Suitable bases are, in particular, tertiary amines such as trialkylamines, pyridines and dialkyl anilines, and also hydroxides, oxides, carbonates and bicarbonates of alkali metals and alkaline earth metals, as well as alkali metal alcoholates, e.g. potassium tert-butylate and sodium methylate.

The processes are conveniently carried out in the temperature range from −10° to 150° C., preferably from 20° to 80° C., under normal or slightly elevated pressure (up to 5 bar.) and preferably in the presence of a solvent or diluent which is inert to the reactants.

Examples of suitable solvents or diluents are: ethers and ethereal compounds such as diethyl ether, diisopropyl ether, dioxane and tetrahydrofurane; and ketones such as acetone, methyl ethyl ketone and cyclohexanone.

The starting materials of the formula III are known and can be obtained by known methods. The starting materials of the formula II are novel. They can be obtained by known methods and also constitute an object of the invention.

The compounds of formula I are suitable for controlling a variety of pests of animals and plants. Accordingly, they can be used for controlling all development stages of insects, for example of the orders Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera. They also have a good fungicidal action. In particular, however, the compounds of formula I are suitable for controlling mites which are parasites of plants and animals, and for controlling ticks of the order Acarina.

The compounds of the formula I are used in unmodified form or, preferably, together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. The methods of application, such as spraying, atomising, dusting, scattering or pouring, are chosen in accordance with the intended objectives and the prevailing circumstances, just like the nature of the compositions.

The formulations, i.e. the compositions or preparations containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane, or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidised vegetable oils such as epoxidised coconut oil or soybean oil; or water.

The solid carriers used e.g. for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethylanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyoxyethylene adducts, tributylphenoxypolyethoxyethanol, polyethylene glycol and octylphenoxypolyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual," MC Publishing Corp., Ringwood, N.J., 1979.

The pesticidal formulations usually contain 0.1 to 99%, preferably 0.1 to 95%, of a compound of the formula I, 1 to 99.9% of a solid or liquid adjuvant, and 0 to 25%, preferably 0.1 to 25%, of a surfactant.

Whereas commercial products are preferably formulated as concentrates, the end user will normally employ dilute formulations.

The formulations can also contain further additives such as stabilisers, antifoams, viscosity regulators, binders, adhesives, as well as fertilisers or other active ingredients, in order to produce special effects.

FORMULATION EXAMPLES

Formulation examples using liquid active ingredients of the formula I (throughout, percentages are by weight)

| (1) Emulsifiable concentrates | (a) | (b) | (c) |
|---|---|---|---|
| active ingredient | 20% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexanone | — | 15% | 20% |
| xylene mixture | 70% | 25% | 20% |

Emulsions of any required concentration can be produced from such concentrates by dilution with water.

| (2) Solutions | (a) | (b) | (c) | (d) |
|---|---|---|---|---|
| active ingredient | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20% | — | — |
| epoxidised coconut oil | — | — | 1% | 5% |
| petroleum fraction (boiling range 160–190°) | — | — | 94% | — |

These solutions are suitable for application in the form of microdrops.

| (3) Granulates | (a) | (b) |
|---|---|---|
| active ingredient | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| (4) Dusts | (a) | (b) |
|---|---|---|
| active ingredient | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

Formulation examples using solid active ingredients of the formula I (throughout, percentages are by weight)

| (5) Wettable powders | (a) | (b) |
|---|---|---|
| active ingredient | 20% | 60% |
| sodium lignosulfonate | 5% | 5% |
| sodium laurylsulfate | 3% | — |
| sodium diisobutylnaphthalenesulfonate | — | 6% |
| octylphenol polyethylene glycol ether (7–8 moles of ethylene oxide) | — | 2% |
| highly dispersed silicic acid | 5% | 27% |
| kaolin | 67% | — |

The active ingredient is thoroughly mixed with the adjuvants and the mixture is thoroughly ground in a suitable mill, affording wettable poweders which can be diluted with water to give suspensions of the desired concentration.

| (6) Emulsifiable concentrate | |
|---|---|
| active ingredient | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| (7) Dusts | (a) | (b) |
|---|---|---|
| active ingredient | 5% | 8% |
| talcum | 95% | — |
| kaolin | — | 92% |

Dusts which are ready for use are obtained by mixing the active ingredient with the carriers, and grinding the mixture in a suitable mill.

| (8) Extruder granulate | |
|---|---|
| active ingredient | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| (9) Coated granulate | |
|---|---|
| active ingredient | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| (10) Suspension concentrate | |
|---|---|
| active ingredient | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

EXAMPLE 1

(a) Preparation of the starting material of the formula

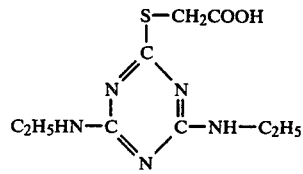

27.7 g of thioglycolic acid and then 60.7 g of triethylamine are added dropwise, at 70° C., to a solution of 60.5 g of simazin in 500 ml of dimethyl formamide. The reaction mixture is stirred for 2 hours at 70° C., then the volatile constituents are removed in vacuo and the residue is taken up in 500 ml of ethyl ether. Precipitated solid is removed by filtration and the filtrate is heated for 1 hour to 80° C./$10^{-2}$ mb. Recrystallisation from methanol/water (5:1) yields the title compound with a melting point of 104° to 106° C.

(b) Preparation of the final product of the formula

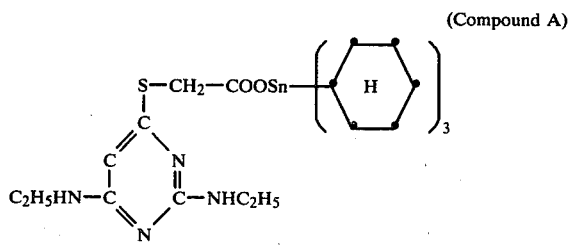

(Compound A)

25.7 g of the compound of the formula

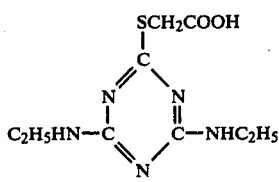

and 35.7 g of tricyclohexyl tin hydroxide are heated to reflux in 100 ml of toluene, while removing the water of reaction. The volatile constituents are removed in vacuo, leaving as residue a viscous oil which solidifies on cooling.

Yield: 59.1 g of compound A, which has a melting point of 116°–118° C. after recrystallisation from isopropanol.

The following compounds are also obtained in analogous manner:

IR spectrum in CDCl$_3$: $c_D$: 1550 cm$^{-1}$ (salt bands).

(Compound C)

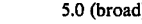

(Compound D)
m.p. 77–81° C.

EXAMPLE 2

(a) Preparation of the starting material of the formula

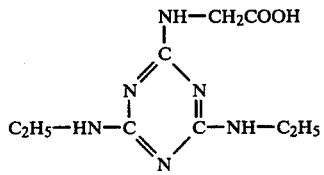

45 g of glycine and 121 g of triethylamine are added to 800 ml of dimethyl acetate at 70° C. With stirring, 101 g of simazin are added in portions and the mixture is then heated for 24 hours at 140° C. After the mixture has cooled, the solids are removed by filtration. To the clear filtrate are first added, at 20° C., 250 ml of conc. hydrochloric acid and then aqueous sodium hydroxide until the onset of clear alkaline reaction. The greasy brown precipitate is removed by filtration and glacial acetic acid is added to the filtrate until the onset of weakly acid reaction. The colourless precipitate is isolated by filtration and dried, affording the title compound in the form of a crystalline powder, the HMR spectrum of which accords with the structural formula.

(b) Preparation of the starting material of the formula

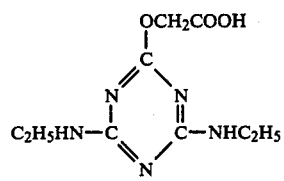

45 g of glycine and 121 g of triethylamine are added at 70° C. to 800 ml of dimethyl acetate. With stirring, 101 g of simizin are added in portions and the mixture is then heated for 24 hours at 140° C. After the mixture has cooled, the solids are removed by filtration and the filtrate, to which 400 ml of conc. hydrochloric acid and 1 liter of water are added at 20° C., is made alkaline with aqueous sodium hydroxide and filtered. The batch is acidified with glacial acetic acid and concentrated. The residue is dissolved in 150 ml of chloroform and the solution is extracted three times with water. The aqueous extract is dried and chromatographed on silica gel with chloroform as eluant, affording the title compound in the form of a pale yellow oil, the HMR spectrum of which accords with the structural formula.

(c) Preparation of the final products 0.3 g of the compound of the formula

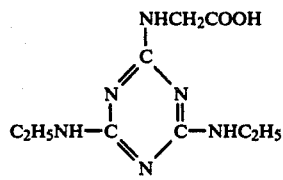

and 4.8 of tricyclohexyl tin hydroxide are heated to reflux in 50 ml of toluene, while removing the water of reaction. The solution is concentrated in vacuo and precipitated solid is removed by filtration after addition of diethyl ether. The filtrate is taken up in acetone and, after the addition of water, the colourless precipitate is isolated by filtration and dried, affording the compound of the formula

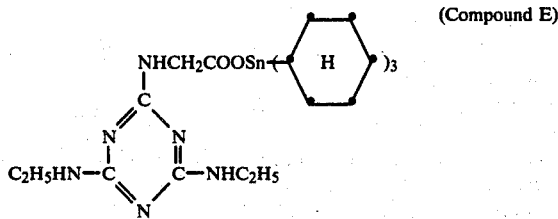

(Compound E)

with a melting point of 95°–98° C.
The compound of the formula

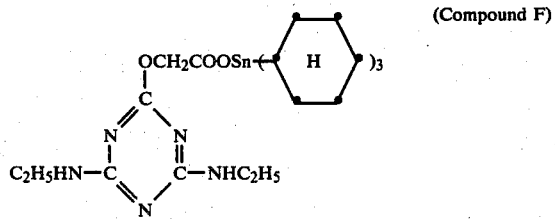

(Compound F)

with a melting point of 72°–75° C., is obtained in analogous manner, but using the intermediate prepared in (b).

EXAMPLE 3

Activity against plant-destructive acarids: Tetranychus urticae (OP-sensitive) and Tetranychus cinnabarinus (OP-resistant)

16 Hours before the start of the test for acaricidal activity, the primary leaves of Phaseolus vulgaris plants are infected with infested pieces of leaf from a mass culture of Tetranychus urticae (OP-sensitive) and Tetranychus cinnabarinus (OP-resistant). One plant is used for each species and concentration. The pieces of leaf are then removed from the plants, which have become populated with eggs, larvae and adults of the test mites. Using a dilution series of 50, 100, 200 and 400 ppm of active ingredient, the plants are sprayed dripping wet with a solution or aqueous emulsion of the compound to be tested, prepared from a 25% emulsifiable concentrate. During the entire test run the plants are kept in greenhouse compartments at 25° C. The test is evaluated 2 and 7 days after application by making a mortality count of eggs (after 7 days) and of larvae and adults (after 2 and 7 days). The results (percentage kill) are reported in the following table.

| Compound | Stage | Tetranychus urticae | | | | Tetranychus cinnabarinus | | | |
| | | 2 days | | 2 days | | 2 days | | 7 days | |
| | | K | C | K | C | K | C | K | C |
|---|---|---|---|---|---|---|---|---|---|
| A | adults | 100 | 100 | 100 | 50 | 100 | 100 | 100 | 100 |
|   | larvae | 100 | 100 | 100 | 50 | 100 | 100 | 100 | 100 |
|   | eggs |   |   | 80–99 | 400 |   |   | 80–99 | 400 |
| B | adults | 100 | 100 | 100 | 100 | 100 | 100 | 100 | 100 |
|   | larvae | 100 | 100 | 100 | 100 | 100 | 100 | 100 | 100 |
|   | eggs |   |   | 80–99 | 200 |   |   | 60–79 | 400 |

K = percentage kill
C = concentration in ppm

What is claimed is:
1. A triorgano-tin triazine compound of the formula

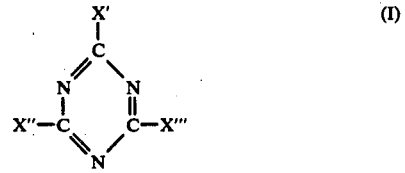

(I)

wherein X' is $-S-Y-COOSn(R')_3$, $-O-Y-COOSn(R')_3$ or $-NH-Y-COOSn(R')_3$, each of X" and X''' has the same meaning as X' or is halogen, $(C_1-C_6\text{alkyl})_2N-$, $(C_1-C_6\text{alkyl})-NH-$, $(C_1-C_6\text{alkyl})-O-$ or $(C_1-C_6\text{alkyl})-S-$, Y is $C_1-C_6$alkylene, and the radicals R' can be the same or different and are $C_1-C_6$alkyl, benzyl, phenyl or cyclohexyl, each of which is unsubstituted or substituted by halogen, $C_1-C_4$alkyl, $C_1-C_4$alkoxy or trifluoromethyl.

2. A compound according to claim 1, wherein X' is $-S-Y-COOSn(R')_3$, each of X" and X''' is $(C_1-C_6\text{alkyl})-NH-$, Y is methylene and R' is n-butyl, phenyl or cyclohexyl.

3. A compound according to claim 1, wherein X' is $-S-Y-COOSn(R')_3$, each of X" and X''' is $(C_1-C_6\text{alkyl})-NH-$, Y is methylene and R' is cyclohexyl.

4. The compound according to claim 3 of the formula

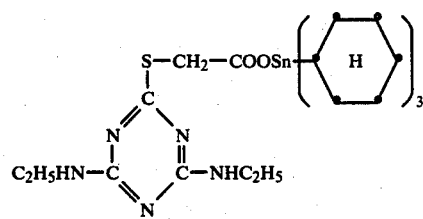

5. The compound according to claim 3 of the formula

6. The compound according to claim 2 of the formula

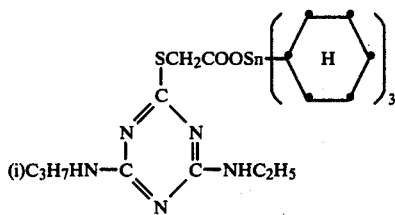

7. The compound according to claim 2 of the formula

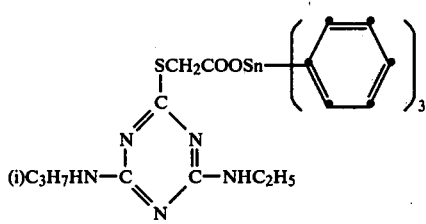

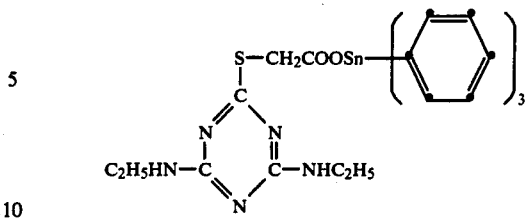

8. A composition for combatting insects, fungi or acarids, which composition contains (1) as active component, a compound according to claim 1, and (2) a carrier.

9. A method of controlling insects, fungi or acarids harmful to animals or plants at a locus, which comprises applying to said locus a specifically effective amount of a compound according to claim 1.

10. A method according to claim 9, wherein acarids are controlled.

11. A compound of the formula

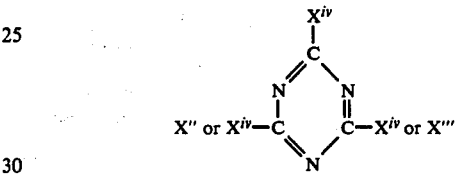

wherein $X''$ and $X'''$ are halogen, the radicals $-S-Y-COOSn(R')_3$, $-O-Y-COOSn(R')_3$, $-NH-Y-COOSn(R')_3$, $(C_1-C_6alkyl)_2N-$, $(C_1-C_6alkyl)-NH$, $(C_1-C_6alkyl)-O-$ or $(C_1-C_6alkyl)-S-$, $X^{iv}$ is $-S-Y-COOH$, $O-Y-COOH$ or $-NH-Y-COOH$, Y is $C_1-C_6alkylene$, and the radicals R' can be the same or different and are $C_1-C_6alkyl$, benzyl, phenyl or cyclohexyl, each of which is unsubstituted or substituted by halogen, $C_1-C_4alkyl$, $C_1-C_4alkoxy$ of trifluoromethyl.

12. A compound according to claim 11, which contains the radicals $X''$, $X'''$ and $X^{iv}$.

* * * * *